United States Patent [19]

Wolf et al.

[11] Patent Number: 5,153,131
[45] Date of Patent: Oct. 6, 1992

[54] HIGH ASPECT REACTOR VESSEL AND METHOD OF USE

[75] Inventors: David A. Wolf; Clarence F. Sams, both of Houston; Ray P. Schwarz, Friendswood, all of Tex.

[73] Assignee: The United States of America as represented by the Administrator of the National Aeronautics and Space Administration, Washington, D.C.

[21] Appl. No.: 625,345

[22] Filed: Dec. 11, 1990

[51] Int. Cl.⁵ .......................... C12N 5/02; C12M 3/06; C12M 3/02
[52] U.S. Cl. .................... 435/240.240; 435/240.25; 435/284; 435/286; 435/311; 435/312; 435/313; 435/315
[58] Field of Search ........... 435/240.2, 240.23, 240.24, 435/240.241, 240.242, 240.25, 284–286, 311, 312, 313, 315, 818; 261/83, 87, 92, DIG. 28, 122; 210/321.64, 321.67, 321.68, 321.75, 321.84; 422/45, 48

[56] References Cited

U.S. PATENT DOCUMENTS

| | | | |
|---|---|---|---|
| 3,676,074 | 6/1972 | Shibayama et al. | 435/312 |
| 4,264,739 | 4/1981 | Grabner et al. | 435/241 |
| 4,310,630 | 1/1982 | Girard et al. | 435/284 |
| 4,343,904 | 8/1982 | Birch et al. | 435/240 |
| 4,537,860 | 8/1985 | Tolbert et al. | 435/240 |
| 4,605,626 | 8/1986 | Beck | 435/291 |
| 4,649,117 | 5/1987 | Familletti | 435/313 |
| 4,661,458 | 6/1987 | Berry et al. | 435/284 |
| 4,680,266 | 7/1987 | Tschopp et al. | 435/284 |
| 4,693,983 | 9/1987 | Davies et al. | 435/284 |
| 4,762,794 | 8/1988 | Nees | 435/284 |
| 4,988,623 | 1/1991 | Schwarz et al. | 435/284 |
| 5,026,650 | 6/1991 | Schwarz et al. | 435/286 |

FOREIGN PATENT DOCUMENTS

| | | |
|---|---|---|
| 0112154 | 6/1984 | European Pat. Off. . |
| 0164888 | 10/1985 | European Pat. Off. . |
| 9005179 | 5/1990 | PCT Int'l Appl. ................. 435/284 |

OTHER PUBLICATIONS

"The Clinostat-A Tool for Analysing the Influence of Acceleration on Solid-Liquid Systems," W. Briegleb, *Proceedings of a Workshop on Space Biology*, Cologne, Germany, Mar. 11, 1983 (ESASP-206, May 1983). pp. 97–101.

"Particle Orbits in a Rotating Liquid," William W. Fowlis and Dale M. Kornfeld, *Space Science Laboratory*, NASA Marshall Space Flight Center, Huntsville, Ala. 35812 and Glyn O. Roberts, Roberts Associates, Inc., 1726 Pine Valley Dr., Vienna, Va. 22180.

"The Large-Scale Cultivation of Mammalian Cells," Joseph Feder and William R. Tolbert, *Scientific American*, Jan. 1983, vol. 248, #1, pp. 36–43.

"Gravisensitivity of the Acellular Slime Mold Physarum Polycephalum Demonstrated on the Fast-Rotating Clinostat," Ingrid Block & Wolfgang Briglep, *European Journal of Cell Biology* 41, pp. 44–50, 1986.

*Primary Examiner*—Robert J. Warden
*Assistant Examiner*—William H. Beisner
*Attorney, Agent, or Firm*—Russell E. Schlorff; Guy M. Miller; Edward K. Fein

[57] ABSTRACT

A suspension cell culture system where a culture chamber is rotatable about a horizontal axis and has a vertical large area oxygen transmissible membrane spaced a distance about 0.25 inches less than 1.0 inches from a facing vertical wall surface for effective transmission of oxygen to cells in suspension in the culture chamber. The facing vertical wall surface can be a dialysis membrane for exchange of fresh nutrient from a dialysis chamber with cell waste product in the culture chamber.

25 Claims, 2 Drawing Sheets

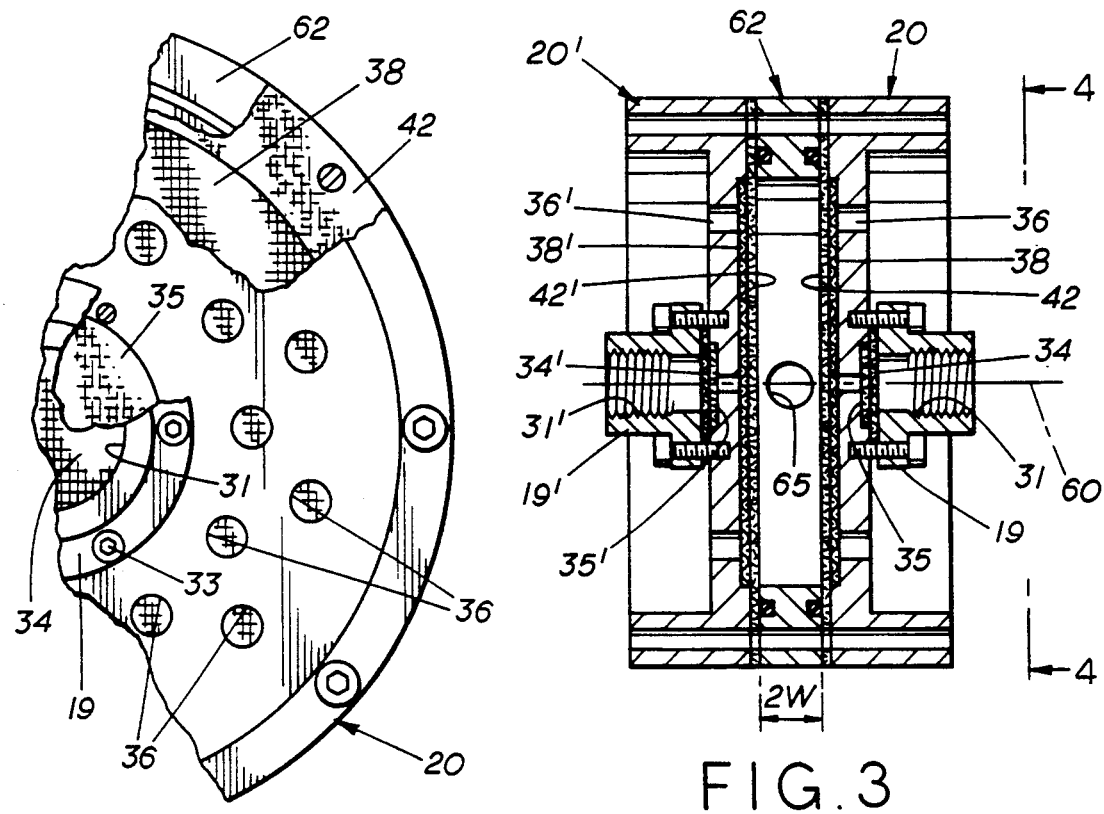
FIG. 4
FIG. 3
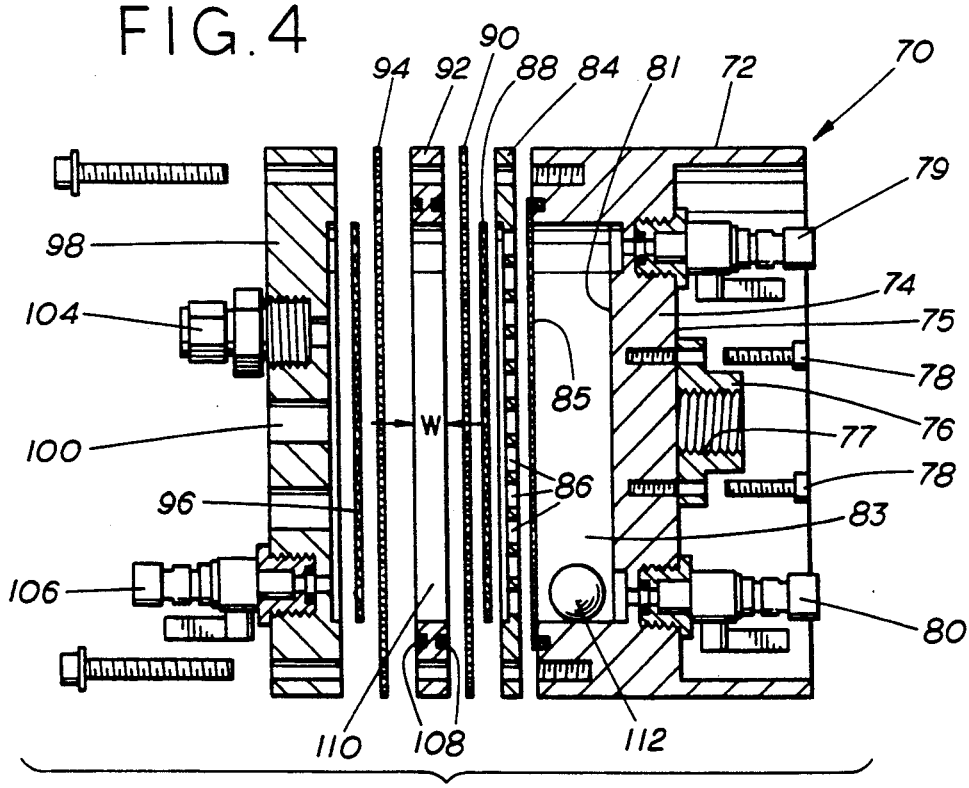
FIG. 5

HIGH ASPECT REACTOR VESSEL AND METHOD OF USE

ORIGIN OF THE INVENTION

The invention described herein was made in the performance of work under a NASA contract and is subject to provisions of Section 305 of the National Aeronautics and Space Act of 1958, Public Law 85-568 (72 Stat. 435; 42 U.S.C. 2457).

RELATED APPLICATIONS

This application has subject matter related to the subject matter disclosed in the U.S. patent application Ser. No. 07-213559, filed Jun. 30, 1988 (MSC-21293-1) now U.S. Pat. No. 4,988,623; Ser. No. 07-213558, filed Jun. 30, 1988 (MSC-21294-1) now U.S. Pat. No. 5,026,650.

FIELD OF THE INVENTION

The present invention relates to an improved bio-reactor vessel and system which are useful for carrying out mammalian cell growth in suspension in a culture media.

BACKGROUND OF THE INVENTION

Bacterial cell culture processes have been developed for the growth of single cell bacteria, yeast and molds which can be characterized as encased with a tough cell wall. Large scale culture of bacterial type cells is highly developed and such culture techniques are less demanding and are not as difficult to cultivate as mammalian cells. Bacterial cells can be grown in large volumes of liquid medium and can be vigorously agitated without any significant damage.

Mammalian cell culture, however, is much more complex because such cells are more delicate and have a more complex nutrient requirement for development. Mammalian cells cannot withstand excessive turbulent action without damage to the cells and must be provided with a complex nutrient medium to support growth.

In co-pending application, Ser. No. 07-213558, filed Jun. 30, 1988 (MSC-21293-1) and Ser. No. 07-213558, filed Jun. 30, 1988 (MSC-21294-1), systems are shown where mammalian cells are grown in a culture media containing micro-beads and the cells attach to the beads which are suspended in a culture media.

In each such system a culture media is contained in an elongated cylindrical member which is rotated slowly about a horizontal axis while dissolved oxygen was permeated through an elongated annular permeation member for replenishing oxygen in the culture media. While such systems have provided excellent results for cells which attach to microbeads in order to grow, it was found that there was difficulty in culturing cells in suspension without microbeads. It was discovered that the oxygen transmission into the culture media is so slow that effective cell growth does not occur in an annular volume spaced as much as one inch from the permeation member. If agitation is introduced to the system to assist the oxygen transmission, the agitation is counterproductive to cell growth and free aggregation of suspension type cells in that the cells are damaged and disruptive mechanical forces are introduced. Thus, the volume and spatial arrangement of cell growth obtained in such agitated suspension systems has been limited.

In summary, while bio-reactors used to culture mammalian cells utilize mechanical parts, air or fluid movement as a lift mechanism to achieve particle suspension, such mechanisms induce damage and disruptive forces to growing suspension type cells or 3-dimensional cellular structures such as tissues either directly or indirectly by fluid shear.

Prior Art

In addition, the prior art known to applicants include the following:

Paper entitled, "The Clinostat—A Tool For Analyzing The Influence Of Acceleration On Solid-Liquid Systems" by W. Briegleb, published by the proceedings of a workshop on Space Biology, Cologne Germany, on Mar. 11, 1983 (ESASP-206, May 1983). In this paper, clinostat principals are described and analyzed relative to gravity affects. Some clinostat experiments are described including experiments where cultures are grown within cylinders which are rotated about a horizontal axis.

Paper entitled, "Particle Orbits In A Rotating Liquid", by William W. Fowlis and Dale M. Kornfeld, a Nasa white paper planned for publication. The Nasa paper discloses use of latex microspheres up to 3 micrometers in diameter in a rotating reactor cylinder where the cylinder is rotated about a horizontal axis to keep the particles in suspension. The rotation of the reactor cylinder maintains the particles in suspension without agitation to cause particle collision which would result in flocculation.

U.S. Pat. No. 3,676,074 relates to an apparatus for treating organic waste where a cylinder is rotated about a stationary horizontal pipe which has a central air input for supplying an air input to the waste material.

U.S. Pat. No. 4,537,860 which relates to a static or stationary system for cell culture of animal cells where the cells in the vessel are supplied with a nutrient 21 which passes through a porous tube 19 into the matrix (with cells) and that exits through passages 24 and 25. Oxygen is passed through a permeable membrane 25.

U.S. Pat. No. 4,310,630 relates to a stationary or static cell culture growth device. In the '630 patent, the patentee proposes to have a rotating cylinder about a horizontal axis which is rotatable between 5 and 20 RPM. Included within the vessel is a matrix of tubular elements 11 for providing increased surface area for growth of cells. Not all of the elements 11 are covered with nutrient and the gas is supplied through one inlet and exited through an outlet.

In U.S. Pat. No. 4,605,626, an electrode assembly 16 is rotated about a vertical axis and inert gas is passed through a gas sparger 26 for dispersal as bubbles into a bacteria solution 14. The shaft rotates and agitates while the chamber remains static.

U.S. Pat. No. 4,264,739 relates to a sparger for a mass cell culture system which is comprised of an elongated tube having a plurality of ports.

U.S. Pat. No. 4,343,904 relates to growth of animal cells and a vertical cylindrical vessel having spaced apart plates on an axial shaft. An external pumping loop is provided for circulating the contents of the vessel from the bottom to the top of the vessel. Cell growth is carried out by substantially filling the vessel with cells and growth medium and allowing the cells to settle onto disk surfaces and rotating the shaft while circulating the vessel contents from the bottom to the top for mixing.

U.S. Pat. No. 4,649,117 discloses an air lift bioreactor for maintaining cells in suspension and includes a centrally located gas inlet means at the lower end of the mixing chamber, a conical side wall in the growth chamber and introducing an oxygen containing gas to bubble up through the cells and liquid medium to carry the cells and liquid medium upward from the mixing chamber to the growth chamber and so that the cells and liquid medium flow downwardly along the conical side wall to replace the cells and liquid medium being carried upwards in the mixing chamber. The system is for agitating the cells while minimizing shear forces.

A paper entitled, "The Large Scale Cultivation of Mammalian Cells", by Joseph Feder and William R. Tolbert, published in the Scientific American Magazine, January 1983, Vol. 248, No. 1, pps. 36-43. In this paper, agitation of the cells is described as required to keep the cells suspended in the medium and describes a turbine agitator, a marine propeller agitator, and a vibro mixer for mixing. The paper also describes a perfusion reactor in which an agitation is provided by four slowly rotating flexible sheets of monofilament nylon which are rotated about a vertical axis while the medium in the main vessel is continuously pumped to the satellite filter vessel. The filter retains the cells which are pumped along with the remainder medium back into the vessel for further proliferation.

A paper entitled, "Gravinsensitivity Of The Acellular, Slime, Mold, Physarum, Polycephalum Demonstrated On The Fast Rotating Clinostat", by Ingrid Block and Wolfgang Brigleb, published in the European Journal of Cell Biology 41, pps. 44-50, 1986. This paper describes rotation of a culture vessel about a horizontal axis for the simulation of weightlessness. The paper is a study relative to the gravity influences in the control systems of cells.

U.S. Pat. No. 4,661,458—This patent discloses a culture vessel designed to minimize the diffusion distance to that found in human tissue. The inventor mentions the negative aspects of introducing a mixing element and accomplishes high density cultures by means of plural diffusion capillaries. The typical maximum distance between a capillary and cell tissue is less than 200 microns. Pumps are used to continuously circulate nutrients and extractants through the capillaries.

U.S. Pat. No. 4,680,266—This patent discloses a cell culture chamber in which an osmotic fluid pump forces cell culture media or nutrients through a cell chamber.

U.S. Pat. No. 4,693,983—This patent discloses a culture vessel reactor comprising a plurality of support matrices to allow for high density cultures. Each layer has three distinct components, i.e., a culture region, a nutrient supply region, and an extractant region. Every culture region is exposed to at least one nutrient and one extractant region directly. This configuration allows for high concentration, well nourished cultures without mixing.

EPA publication number 0-112154 filed Dec. 13, 1983 by Bio-Response, Inc. discloses a cell production system where a lymph culture medium is continuously flowed across a membrane which separates the lymph from the cells to be cultured.

European Patent 0,164,888 published Dec. 18, 1985 by Japan Synthetic Rubber Co., Ltd relates to cell culture in suspension or on beads where the culture medium is rotated about a horizontal axis. A feed pipe continuously supplies fresh liquid medium to a central axis location and spent medium exits at a remote filter location to an outlet pipe. The input and output of medium is continuous while the chamber is rotated about a horizontal axis.

SUMMARY OF THE PRESENT INVENTION

The purpose of the invention is to grow and maintain cells in suspension in a culture media under a homogeneous distribution under acceptable conditions of gas partial pressures and nutrient levels without introducing direct agitation mechanisms or associated disruptive mechanical forces. Conventional techniques either introduce an agitation mechanism with associated fluid shear stress or allow non-agitated cells to settle into a non-homogeneous distribution in the culture media. The current invention allows growth of suspension cells or aggregations thereof under acceptable environmental conditions for cell growth and function.

In one form of the present invention, a cylindrical member defines a cell culture chamber which is rotatable about an approximately horizontal axis. The culture chamber of the present invention rotates to maintain an even distribution of cells in suspension and minimizes the length of a gas diffusion path to maintain an acceptable biochemical micro-environment for gas partial pressures and nutrient concentrations in the rotating culture chamber.

The cylindrical member is attachable to a motor drive for rotation about its horizontal axis. The cylindrical member which defines the cylindrical shaped culture chamber contains mammalian cells and a nutrient media. The culture chamber has a high diameter (depth) dimension (in a vertical direction) relative to its width dimension (in a horizontal direction) where the width dimension is the gas diffusion path and is a function of transmissibility of oxygen in the nutrient media. The open end of the culture chamber is closed by a circularly shaped flexible permeable member. The permeable member has access through an access passageway in the vessel to an oxygen containing gas so that oxygen is supplied to one side of the permeable member while the other side of the permeable member is in contact with the nutrient media in the culture chamber.

For processing of suspension type cells, the system including the culture chamber is sterilized. Fresh fluid medium and cells are admitted to completely fill the cell culture chamber. Multiple cell types may be introduced in order to take advantage of their interactions. This can be accomplished by use of an inlet valve to the chamber. An oxygen containing gas is admitted to one side of the flexible permeable member or membrane so that dissolved oxygen is passed through the permeable member and into the nutrient media. The cylinder member which defines the culture chamber is rotated at a low speed within an incubator so that the circular motion of the fluid culture media does not create centrifugal forces sufficient to move cells outwardly from the rotational axis yet suspends the cells throughout the culture chamber during the cell growth period in the incubator.

The system thus involves rotating a fluid nutrient medium having zero head space in a culture chamber about a nearly horizontal rotational axis. The rotation of the fluid nutrient medium is controlled to prevent development of adverse centrifugal forces on the cells in suspension. While rotating the fluid nutrient, the medium gas (oxygen) is allowed to exchange across the vertical permeable member or membrane to the fluid nutrient medium where the permeable membrane is disposed across the end of the culture chamber and the chamber has a high diameter to width ratio. The aqueous culture media distorts the flexible permeable membrane because of the weight of the liquid and the hydrostatic pressure on the permeable membrane pushes the permeable membrane tightly against a support screen at the bottom sector of the permeable membrane below the central axis and pushes the permeable membrane less tightly at the top section. This distortion of the permeable membrane is enough to cause mixing of the culture media as the culture chamber is rotated. The width between the side walls of the culture chamber is selected to obtain necessary oxygen transmissibility over the gas diffusion path for cell growth in the space between the side walls of the culture chamber.

In another form of the present invention, the cylindrical culture chamber is closed on one side by the permeable membrane as described above and is closed on an opposite side by a dialysis membrane (or specific molecular weight cut-off filter) which separates the culture chamber from a cylindrical dialysis chamber. In operation, waste products from the culture chamber are exchanged with fresh nutrient media in the dialysis chamber according to the concentration gradients.

The primary mechanical components are the high aspect cell culture chamber, i.e., large diameter to width ratio, the gas exchange chamber, and the dialysate chamber. The cells are introduced through a port leading to the cell culture chamber. The cell culture chamber has a very narrow horizontal width compared to the diameter or vertical dimension. A silicone rubber coated fabric membrane separates the cell culture chamber from the gas exchange chamber allowing diffusion of gases between these chambers in response to gradients induced by the cellular metabolism. The partial pressures of the gas mixture in the gas exchange chamber are controlled by free exchange with the external environment which may be a cell culture incubator or other gas control system. The cell culture chamber is separated from the dialysate chamber by a dialysis membrane or specific molecular weight cut-off filter membrane depending on the experimental purpose. The nutrients and metabolic waste products which are permeable in the separation material are free to exchange according to concentration gradients generated by cellular metabolism. The dialysate chamber should be mixed by some agitation mechanism. A marble rolling within the chamber works well. It is also recommended to perfuse the dialysate chamber or to intermittently exchange its contents to remove waste products or to introduce fresh nutrients.

In all cases of gas, nutrient, and waste product exchange the concentration gradients which drive the exchange are sustained over a sufficient distance to allow the cell chemical micro-environment to remain at desired levels. Products which are desirable to extract from the culture may be extracted from the dialysate without disruption of the cell culture space. Similarly it is possible to introduce soluble materials into the dialysate without disruption of the cell culture space.

It will be appreciated that the invention provides a large vertical permeable surface area and a small horizontal spacing for defining a cell culture chamber for optimum growth of cells in suspension when the chamber is rotated. Virtually all of the horizontal spacing is effectively utilized in cell growth. The culture chamber can be increased in volume if the culture medium is subjected to mixing by a viscous pump or other agitating device because mixing increases the distribution of dissolved gas. This, however, produces a less quiescent culture which can adversely affect cell growth.

It is also possible to utilize a cylindrically shaped inner permeable member to define an interior dialysate space and concentrically dispose a cylindrically shaped outer permeable member for gas permeation where the annulus between the inner and outer permeable members defines a cell culture space. The radial spacing between the inner and outer permeable members is dimensioned in accordance with the present invention.

The advantages of the present invention and its alternate embodiments include the ability to freely suspend suspension cell types and 3-D aggregations of such cells in a homogeneous distribution while simultaneously allowing control over dissolved gas partial pressures and nutrient and waste product concentrations. This allows the cells to freely associate without external mechanical influence over the cells spatial orientations. Minimal damaging fluid shear stresses are present. High viability cultures are obtained and it is possible to handle large numbers of cells with less technical labor. It is possible to sample cells because they are not restrained by a mechanical matrix. This vessel should allow improved research on the interactions of human immune system cells and may well have advantages for the commercial production of monoclonal antibodies. It simulates some aspects of microgravity and is therefore useful for ground based research on the effects of space on cells. It is projected to be of use for cell types which in general may be cultured in suspension or which are cultured on anchorage substrates which do not sediment at a sufficient rate to effect mass transfer. Thus the invention works well for both anchorage dependent or free suspension cells.

DESCRIPTION OF THE DRAWINGS

FIG. 3 is a view in cross section through a modified form of an assembled unit shown in FIG. 2;

FIG. 4 is a view taken along line 4—4 of FIG. 3 with cut away portions for illustrative purposes; and FIG. 5 is a view in cross section and parts in an exploded relationship for illustration for another form of the invention.

DESCRIPTION OF THE PREFERRED EMBODIMENT

Figure 1:
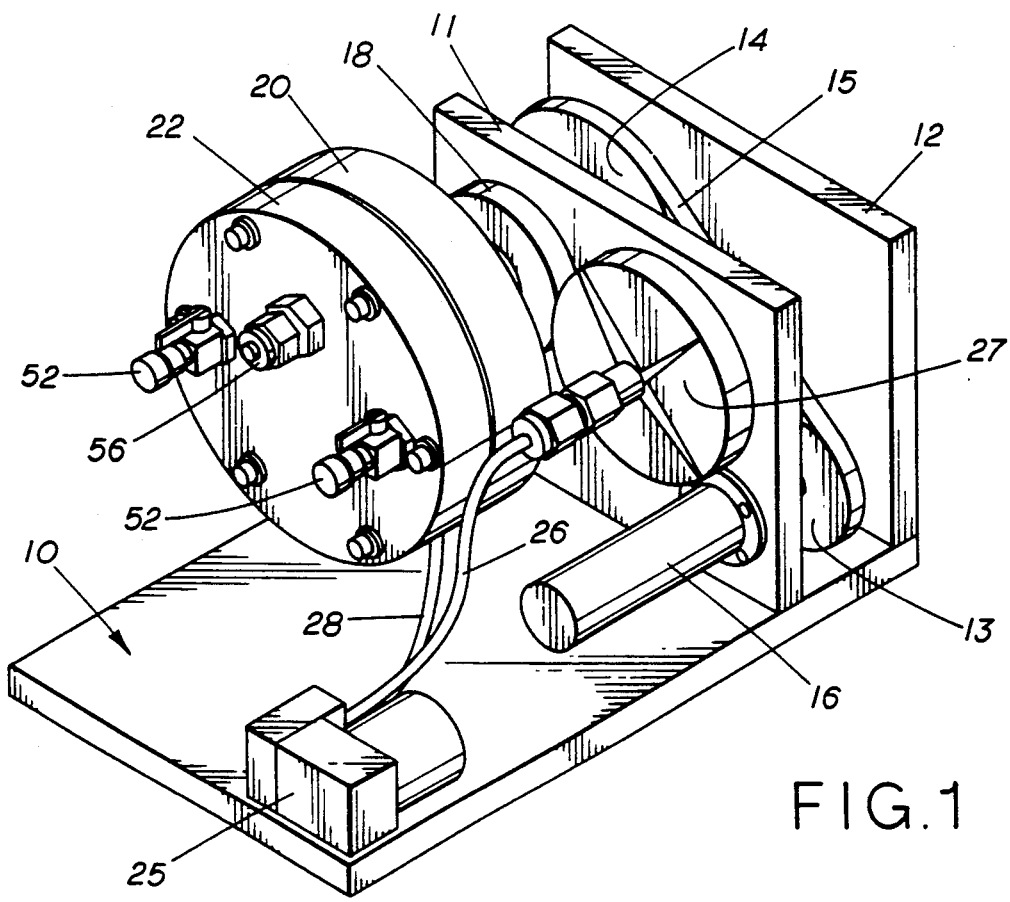
FIG. 1 shows a perspective view of the general organization of the present invention.

Referring now to FIG. 1, the general organization of the present invention is illustrated. A frame means 10 has vertical and spaced apart plates 11,12 which support a motor pulley 13 and a housing pulley 14 with the pulleys 13,14 being connected by a belt drive 15. The motor pulley 13 is coupled to a motor 16 which can be controlled in a well known manner to provide a desired drive speed.

The housing pulley 14 is connected to a drive shaft 17 (see FIG. 2) which extends through a coupling 18 to a cylindrically shaped end housing 20. The end housing 20 is attached to another cylindrically shaped housing 22.

An air pump 25 on the frame means 10 is connected by input tubing 26 to a input air filter 27. An output tubing 28 from the pump 25 is connected to the coupling 18 where the air input is coupled from the stationary coupling 18 (see FIG. 2) to an internal passageway 30 in the drive shaft 17.

Figure 2:
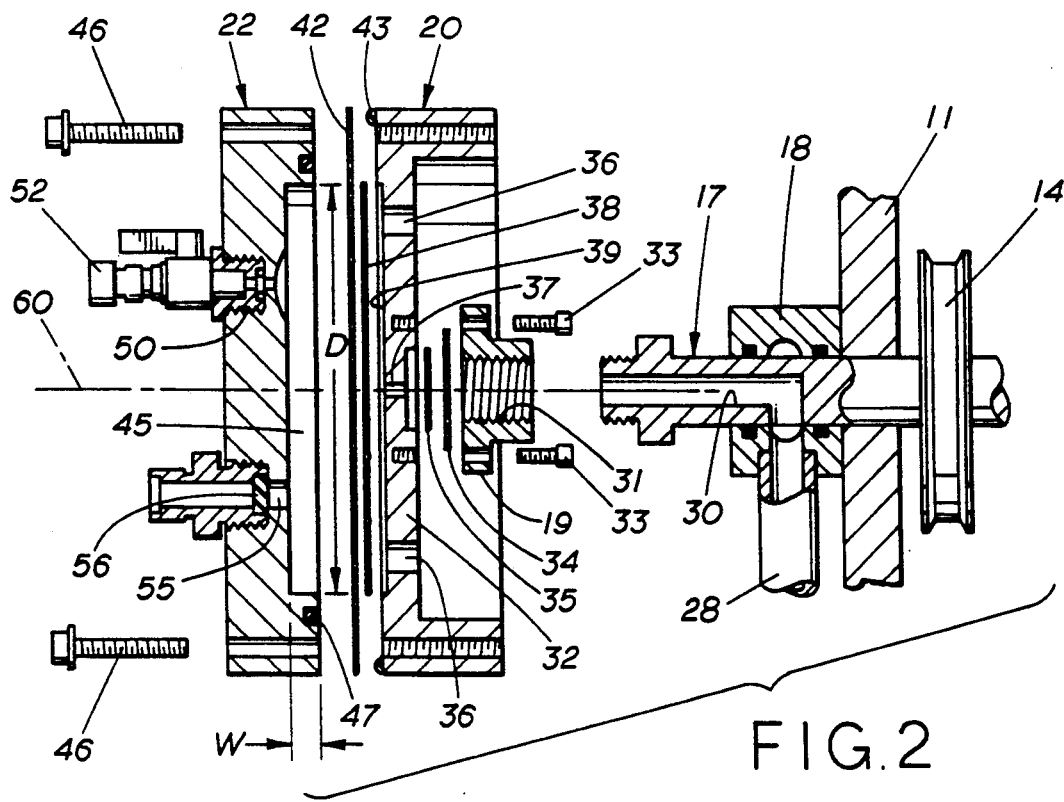
FIG. 2 shows a view in partial cross section of a horizontally rotatable cell culture cylinder member and parts in an exploded relationship.

Referring now to FIG. 2, one form of a cell culture system of the present invention is illustrated in partial cross section where the coupling 18 is attached to the output tubing 28 and the drive shaft 17 has the central air inlet passageway 30 for the passage of air. The drive shaft 17 is threadedly attachable to a coupling hub 19 which has a central opening 31. The coupling hub 19 is centrally attached to a cylindrically shaped, central support plate member 32 by cap screws 33. Disposed across the central opening 31 is a screen support member 34 and a filter cloth 35 which separate the central opening 31 from a central opening 37 in the end housing 20. The screen support member 34 is a fine mesh woven plastic constructed to support the filter cloth 35. The end housing 20 has a plurality of radially and circumferentially disposed openings 36. (See FIG. 4). A circularly shaped screen member 38 is disposed in a cylindrical recess 39 and covers the openings 35,36. A circularly shaped permeable member 42 is disposed over the screen member 38 and is attached by an annular sealing means 43 to the peripheral rim of the end housing 20. The permeable member 42 is constructed from silicone rubber coated fabric.

The housing 22 for the culture chamber 45 is cylindrically shaped and is attached to the end housing 20 with cap screws 46. An O-ring sealing member 47 is disposed between the permeable member 42 and the wall surface of the housing 22. The culture chamber 45 is a cylindrical recess in the housing 22 for holding the culture media and cells.

In the end wall of the housing 22, there are two or more access ports 50, each having a valve operated closure means 52. The access ports permit insertion and removal of liquid from the culture chamber. Another access port 55 can be provided which includes a membrane closure 56. Thus, a hypodermic needle with fluid medium can be inserted through the membrane to inject fluid while fluid is being withdrawn from another port. In this regard samples or media can be withdrawn without forming an air space, thereby preserving a zero head space in the culture chamber.

In use of the present invention, the assembled cylindrical housing assembly is rotated about its central axis 60 while a source of oxygenation (air) is injected through the cylindrical membrane 42. The membrane 42 and the outer wall of the vessel are rotated about the horizontal central axis 60. This involves a type of clinostat principal, i.e., a principal that liquid rotated about a horizontal or nearly horizontal axis can effectively suspend particles in the liquid independent of the effects of gravity.

With respect to the foregoing structure the width "W" of culture chamber is a function of oxygen transmissibility in the culture media while the diameter "D" of the culture chamber is a function of rotationally induced forces. The dimensional ratio of D to W is a high value, for example, six inch diameter to one fourth inch width. As the diameter increases, the effects of centrifugal force limit the diameter dimension. Oxygen transmissibility is a significant factor in cell growth and travels very slowly through the culture media.

It was discovered that oxygen transmissibility or distribution of oxygen in the culture media in an elongated chamber where the oxygen was admitted through a tubular membrane extending along the chamber was inadequate for the growth of suspension type cells in the absence of mixing or stirring. Mixing, however, can be destructive to mammalian cell growth in liquid suspension. It was appreciated that since the oxygen diffusion rate is on the order of one millionth of a centimeter per second, that diffusion of the oxygen in a culture media takes a long time and the partial pressures or the partial pressure gradient of the oxygen in the culture media decreases as a function of distance from the permeation membrane. It was known that cell growth requires absorption or intake of oxygen and that the oxygen intake of a cell is at a reasonably predictable rate. Thus, for a given type of cell having a given rate of oxygen absorption, a cell will not grow if it is too far distant from the permeable membrane or member. Stated another way, cell growth can occur effectively only within a finite spacing or distance from the permeable membrane. This spacing or distance "W" is a finite distance which is a function of the oxygen absorption rate of a cell and the partial pressure of the oxygen at the distance "W" from the oxygen supplied permeable member.

When the cell culture chamber is rotated about a horizontal axis, the diameter of the cell culture chamber and the speed of rotation are factors in the rotational centripetal forces developed in the liquid. In general, the greater the diameter, the slower the rotational speed should be so that the cells remain in suspension and are not distributed to the circular wall surface. At the same time the rotation should be sufficient to maintain the cells in suspension.

It has been experimentally determined that a distance "W" of 0.25 inches and a diameter "D" of 6 inches allows cell growth within the entire volume of the culture chamber at a revolution rate of ten RPM. It has been established that at a distance "W" of 1.0 inches, the oxygen concentration in the culture media is insufficient to support cell growth. While the precise range of "W" has not been ascertained it is less than 1.0 inches from the permeable member.

In another consideration of the dynamics of operation of the present invention, the design enables some mixing and thus increased oxygen transfer by virtue of the large diameter permeable membrane rotated about a horizontal axis. It will be recalled that the permeable membrane is a large flat sheet of silicone rubber coated fabric which is disposed across one end of the cylindrically shaped culture chamber. The permeable membrane is held fixed in place between the circumferential walls of two housing members. When the culture chamber is filled with liquid, the portion of the permeable membrane located below the horizontal axis becomes slightly distorted from the weight of the liquid in the chamber. That is, the permeable membrane is tightly pushed against the support screen at the bottom and is pushed less tightly at the top of the support screen due to hydrostatic pressure of the liquid. The permeable membrane is therefore distorted in much the same manner as a rubber balloon filled with water. The width of the chamber is therefore not uniform and there is a difference in the space width below the horizontal axis and the space width above the horizontal axis. Even though this distortion of the membrane is slight, it is enough to cause a mixing effect on the liquid in the culture chamber when the assembly is rotated. It is estimated that the permeable membrane is displaced 1/20 of an inch at the bottom of the chamber. Therefore, when the assembly is rotated to achieve clinostatic suspension of the culture media, a secondary but critical effect occurs—a mixing effect without shear that enhances the distribution of oxygen (air) throughout the culture media.

As shown in FIG. 3, the distance "W" can be increased or doubled to "2W" by utilizing membranes on both sides of a tubular cylinder housing and utilizing two air sources to provide oxygen to two membranes. Thus, the effective distance is doubled and the volume of culture media and cells can be doubled. As shown in FIG. 3, housings 20 and 20' are mirror image components which are disposed to either side of an annular culture cylinder 60. The culture cylinder has an effective width "2W" which is twice the width "W". A housing 20 or 20' is attached to a central coupling hub 19 or 19'. Air is input through the central opening 31 or 31'. The housings 20, 20' and the cylinder 60 are coupled to one another in an assembly to rotate about a horizontal axis 60. The air input at 31 or 31' passes through a screen support member 34 or 34' and through a filter cloth 35 or 35'. The air passes through a screen 38 or 38' and contacts the cylindrical surface of a membrane 42 or 42'. The air flows out openings 36 or 36'. The cylinder 60 can be provided with one or more peripheral access port means 65 for inputting and outputting liquids.

In the foregoing system, enhanced cell growth is obtained because the oxygen is effectively disseminated to the culture media in the effective distance W relative to the permeable membrane. However, in some instances, the waste products of the cells in the culture chamber accumulate to undesirable concentrations and the nutrients in the culture chamber are deleted before the culture growth process is completed. The following described system provides a means for removing such waste products and providing a source of additional nutrients during incubation.

Referring now to FIG. 5, a dialyzing rotating culture chamber housing 70 is illustrated which will remove waste products from the culture media during incubation. The housing 70 includes a cylindrically shaped end cap housing 72 with a transverse wall 74 located intermediate of its width. On one side 75 of the wall 74 is a centrally located tubular mounting hub 76. The hub 76 is cylindrically shaped with a bore 77 to receive a rotating drive shaft and is attached to the wall 74 by cap screws 78. An intake valve 79 and an outtake valve 80 are located in the wall 74 to selectively input and outtake dialyse solution. The other side 81 of the wall 74 is the end surface for a cylindrical recess 83 which defines a dialysis chamber or dialysate space. Overlying the inner end surface of the end cap housing 72 is a circularly shaped silicon rubber coated fabric membrane 85. The membrane 85 is supported by a spacer member 84 which is constructed from plastic and has a plurality of openings or perforations 86. The spacer member 84 also provides physical support for a cylindrical screen member 88. The screen is a fine mesh woven polypropelene plastic to support a cylindrically shaped permeable membrane 90. The membrane 90 encloses one side surface of an annular culture ring member 92. The other side of the culture ring member 92 is enclosed by a cylindrical permeable membrane 94. The membrane 94 is supported by a support screen member 96 which is received in a cylindrically shaped recess in an end cap housing 98. The recess in the housing 98 is in communication with openings 100 disposed about the housing 98 in locations covered by the screen 96. An inlet valve 104 and an outlet valve 106 are disposed in the cap housing at locations to access the membrane 94. O-rings 106 are provided as necessary for sealing purposes between the various elements.

The width "W" of the culture chamber is about 0.25 inches while the diameter of the chamber is 6 inches. The diameter can be as large as desired so long as the centripetal forces do not adversely affect the cell suspension. On the other hand, the width "W" should be about 0.25 inches and less than 1.0 inches with respect to the oxygen membrane.

In this form of the invention, air is introduced to the space between the membrane 94 and the housing so that oxygen (air) is supplied to the cell culture space 110 and is diffused into the cell culture media. The growth cells in the cell culture space 110 absorb or intake dissolved oxygen and excrete waste product. The excreted waste product exchanges through the dialysis membrane 90 and through the filter 85 with fresh nutrient in the dialysate space according to concentration gradients established by cellular metabolism. In the dialysate space 83, a marble 112 is provided and the rolling marble provides mixing in the dialysate chamber 83. The dialysis exchange enhances the period of incubation which can be used before disturbing or removing cells from the culture chamber.

Cell growth cultures have been successfully produced by use of the present invention in development of human colon carcinoma cells, human embryonic kidney cells, tobacco callus cells, normal human embryonic kerotinocytes cells, normal human colon fibroblast cells, human promyleocytic leukemia cells, bovine embryonic kidney cells, normal embryonic lung cells, mouse melanoma cells, mouse hybridoma cells. As can be appreciated, the ability to grow mammalian cell cultures in a controlled environment is significant.

An example of cell growth in the culture chamber is as follows: mouse myeloma cells (SP2) cells were grown in the culture chamber. First, cell growth medium was loaded into the culture chamber through inlet ports. Care was taken to remove all air bubbles. SP2 cells were injected into the culture chamber so that the concentration of cells was 300,000 cells per milliliter in a 50 milliliter culture chamber volume. The culture chamber was attached to the rotator base and set to rotate at 10 rpm in an incubator. After 72 hours, a sample withdrawn from the sample chamber yielded a cell count of 2.2 million cells per milliliter.

In another experiment, glioma cells were inoculated into the culture chamber at a density of 200,000 cells per milliliter. These cells form spheroidal groups characteristic of their growth. In the culture chamber these spheroids were observed to grow to a large size, 1 and 2 millimeters in diameter.

The clinostatic principle involved is that a fluid rotating (at the appropriate rate) about a horizontal or nearly horizontal axis (with respect to gravity) allows cells to be suspended in a nutrient media.

In the present invention the cell culture chamber is in a cylindrically shaped housing which is rotated about a horizontal axis and the process utilizes zero head space of fluid medium within the culture chamber. The entire cylindrical culture chamber is rotated to suspend the cells by rotation of the culture chamber so that suspension of the cells is such that the cells are not agitated into contact with one another. At the same time the rotational velocity is such that centrifugal forces are not encountered. As a result of the horizontal orientation and the vertical pulsating membrane, a mixing force is developed to move the nutrient media for mixing purposes. The zero head space results in no air bubbles which could cause disruption of fluid streamlines and thus subject the culture to adverse shear effects. The central gas exchange permeable membrane permits a uniform dispersal of component gases from a central core to the fluid medium.

It will be apparent to those skilled in the art that various changes may be made in the invention without departing from the spirit and scope thereof and therefore the invention is not limited by that which is enclosed in the drawings and specifications, but only as indicated in the appended claims.

We claim:

1. A cell culture system for growth of cells in suspension in a liquid culture media comprising:
    a culture housing having a first vertical side wall member, a second vertical side wall member and a cylindrically shaped outer wall therebetween so as to define a culture chamber disposed about a central horizontal axis of said outer wall, said culture chamber being constructed so as to receive cells in suspension in a liquid culture media where the cells have a defined oxygen absorption rate and the culture media has an oxygen transmissibility rate;
    means for revolving said culture chamber about said central horizontal axis;
    said first side wall member being constructed from an oxygen permeable material for permitting permeation of oxygen into the culture chamber from an exterior surface area to an interior surface area of said first side wall member, said first side wall member further constructed and arranged so as to cause a mixing effect on the liquid in the chamber during rotation of the chamber;
    means for accessing oxygen to the exterior surface area of said first side wall member for permeation into said culture chamber; and
    said culture chamber having a width dimension "W" of less than one inch between the interior surface area of said first side wall member and an interior surface of said second side wall member of said culture chamber where said width dimension "W" is a function of the oxygen transmissibility rate in the culture media to delivery oxygen across the width dimension "W" at the oxygen absorption rate of cells disposed in said culture chamber.

2. The culture housing as set forth in claim 1 and further including a circularly shaped porous support member spaced from said first vertical side wall member, said support member having sufficient stiffness for providing back-up support for said first vertical side wall member.

3. The culture housing as set forth in claim 2 wherein said culture housing includes a housing portion constructed so as to mount said support member and said first side wall member, said housing portion containing said means for accessing oxygen which includes a central access port disposed along said central axis and outlet ports dispersed about the surface area of said housing portion.

4. The culture housing as set forth in claim 1 wherein said second side wall member is constructed from an oxygen permeable material for permitting permeation of oxygen into the culture chamber from an exterior surface area to the interior surface area of said second side wall member; and
    wherein the spacing between the interior wall surface areas of said side wall members of said culture chamber is equal to two times the width dimension "W".

5. The culture housing as set forth in claim 1 wherein said width dimension "W" is 0.25 inches.

6. The culture housing as set forth in claim 1 wherein said width dimension "W" is at least 0.25 inches and less than 1.0 inches.

7. The culture housing as set forth in claim 6 wherein the diameter of said culture chamber defined by said cylindrically shaped outer wall is 6 inches or less.

8. A cell culture system for growth of cells or aggregation of cells in suspension in a liquid culture media comprising:
    a culture housing having a first vertical side wall member, a second vertical side wall member and a cylindrically shaped outer wall therebetween so as to define a culture chamber disposed about a central horizontal axis of said outer wall, said culture chamber being constructed so as to receive cells in suspension in a liquid culture media where the cells have a defined oxygen absorption rate and the culture media has an oxygen transmissibility rate;
    means for revolving said culture chamber about said central horizontal axis;
    said first side wall member being constructed from an oxygen permeable material for permitting permeation of oxygen into the culture chamber from an exterior surface area of said first side wall member to an interior surface area of said first side wall member, said first side wall member further constructed and arranged so as to cause a mixing effect on the liquid in the chamber during rotation of the chamber;
    means for accessing oxygen to the exterior surface area of said first side wall member for permeation into said culture chamber;
    said culture chamber having a width dimension "W" of less than one inch between the interior surface areas of said side walls of said culture chamber where said width dimension "W" is a function of the oxygen transmissibility rate in the culture media to deliver oxygen across the width dimension "W" at the oxygen absorption rate of the cells in suspension;
    the second side wall of said culture chamber being constructed from a dialysis material for a dialysis exchange of culture media from an exterior surface area of second side wall to an interior surface area thereof;
    said housing having a cylindrical dialysis chamber disposed adjacent to the exterior surface area of said second side wall where said dialysis chamber contains a dialysate for exchange of waste material generated in said culture chamber with fresh nutrient from said dialysis chamber.

9. The cell culture system as set forth in claim 8 wherein said dialysis chamber contains of means for mixing the contents said dialysis chamber during rotation of said chamber.

10. The cell culture system as set forth in claim 9 wherein said means for mixing is a spherically shaped member which rolls in said dialysis chamber during rotation.

11. The cell culture system as set forth in claim 9 wherein said dialysis material is a molecular filter.

12. The cell culture system as set forth in claim 8 wherein said width dimension "W" is at least 0.25 inch and is less than 1.0 inch.

13. A method for growing cells in suspension or on anchorage substrates, of same or multiple cell types, as single free cells of 3-D aggregations in a culture medium comprising the steps of:
providing a liquid culture media and cells in a cylindrical culture chamber having a width dimension "W" in a transverse horizontal direction of not less than 0.25 inch and not more than 1.0 inch and vertical wall members where one of said wall members is made of oxygen permeable material and has a circular interior wall surface with a diameter which is related to the rotational speed of the liquid culture about a horizontal axis for said wall surface, the cells and the culture media to be less than centripetal forces required to displace cells toward the circumference of said culture chamber;
rotating said culture chamber about the horizontal axis for said wall surface at a rotational rate less than required to precipitate cells by centrifugal force toward the circumference of said culture chamber and sufficient for maintaining cells in suspension while supplying oxygen to said one wall member for transmission to said culture media; and
maintaining the rotation of said culture chamber while supplying oxygen while said culture chamber is in an incubator for cell growth in suspension in said culture chamber.

14. The method as set forth in claim 13 wherein said width dimension "W" is approximately 0.25 inch.

15. The method as set forth in claim 13 wherein the other of said wall members is a dialysis membrane separating said culture chamber from a dialysis chamber containing a dialysate, and disposing of waste products from said culture chamber and replacing such waste products with fresh nutrient by dialysis with said dialysis chamber.

16. The method as set forth in claim 13 wherein said cells are mammalian cells.

17. A method for growing cells in suspension in a culture medium comprising the steps of:
providing a liquid culture media and mammalian cells in a cylindrical culture chamber having a width dimension "W" in a transverse horizontal direction of less than one inch and vertical wall members where one of said wall members is made of oxygen permeable material and has a circular interior wall surface with a diameter which is related to the rotational speed of the liquid culture about a horizontal axis for said wall surface, the cells and the culture media to be less than centripetal forces required to displace cells toward the circumference of said culture chamber;
rotating said culture chamber about the horizontal axis for said wall surface at a rotational rate less than required to precipitate cells by centrifugal force toward the circumference of said culture chamber and sufficient for maintaining cells in suspension while supplying oxygen to said one wall member for transmission to said culture media; and
maintaining the rotation of said culture chamber while supplying oxygen while said culture chamber is in an incubator for cell growth in suspension in said culture chamber.

18. The method as set forth in claim 17 wherein said width dimension "W" is at least 0.25 inch and less than 1.0 inch.

19. The method as set forth in claim 17 wherein the other of said wall members is a dialysis membrane separating said culture chamber from a dialysis chamber containing a dialysate, and disposing of waste products from said culture chamber and replacing such waste products with fresh nutrient by dialysis with said dialysis chamber.

20. A cell culture system for growth of cells in suspension in a liquid culture media comprising:
a culture housing having a first vertical side wall member, a second vertical side wall member and a cylindrically shaped outer wall therebetween so as to define a culture chamber disposed about a central horizontal axis of said outer wall, said culture chamber being constructed so as to receive cells in suspension in a liquid culture media where the cells have a defined oxygen absorption rate and the culture media has an oxygen transmissibility rate;
means for revolving said culture chamber about said central horizontal axis;
said first side wall member being from an oxygen permeable material for permitting permeation of oxygen into the culture chamber from an exterior surface area of said first side wall member to an interior surface area of said first side wall member;
means for accessing oxygen to the exterior surface area of said first wall member for permeation into said culture chamber; and
said culture chamber having a width dimension "W" of less than one inch between the interior surface area of said first wall member and the other wall of said culture chamber where said width dimension "W" is a function of the oxygen transmissibility rate in the culture media to deliver oxygen across the width dimension "W" at the oxygen absorption rate of cells disposed in said culture chamber.

21. The culture housing as set forth in claim 20 wherein said second side wall member is constructed from an oxygen permeable material for permitting permeation of oxygen into the culture chamber from an exterior surface area to the interior surface area of said second side wall member; and
wherein the spacing between the interior wall surface areas of said side wall members of said culture chamber is equal to two times the width dimension "W".

22. The culture housing as set forth in claim 20 wherein said width dimension "W" is 0.25 inch.

23. The culture housing as set forth in claim 20 wherein said width dimension "W" is at least 0.25 inch and less than 1.0 inch.

24. The cell culture system as set forth in claim 20 wherein said second wall is a dialysis membrane separating said culture chamber from a dialysis chamber containing a dialysate for providing by dialysis fresh nutrient to said culture chamber and receiving waste products from said culture chamber.

25. The cell culture system as set forth in claim 24 wherein said dialysis chamber further includes means for mixing said dialysate.

* * * * *